(12) United States Patent
Thiel et al.

(10) Patent No.: US 8,160,334 B2
(45) Date of Patent: Apr. 17, 2012

(54) METHOD FOR OPTICAL MEASUREMENT OF OBJECTS USING A TRIANGULATION METHOD

(75) Inventors: Frank Thiel, Ober-Ramstadt (DE); Joachin Pfeiffer, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 147 days.

(21) Appl. No.: 12/780,511

(22) Filed: May 14, 2010

(65) Prior Publication Data

US 2010/0284589 A1    Nov. 11, 2010

Related U.S. Application Data

(63) Continuation of application No. PCT/EP2008/065627, filed on Nov. 14, 2008.

(30) Foreign Application Priority Data

Nov. 15, 2007   (DE) .......................... 10 2007 054 907

(51) Int. Cl.
  *G06K 9/00*   (2006.01)
(52) U.S. Cl. ........................................ 382/128; 382/206
(58) Field of Classification Search .................. 382/128, 382/131, 130, 149, 145, 199, 506; 702/150; 348/157, 76, 66, 77; 356/511, 603, 73
See application file for complete search history.

(56) References Cited

U.S. PATENT DOCUMENTS

| | | | |
|---|---|---|---|
| 4,615,678 A | 10/1986 | Moermann et al. | 433/201.1 |
| 5,135,308 A * | 8/1992 | Kuchel | 356/604 |
| 5,946,645 A | 8/1999 | Rioux et al. | 702/155 |
| 6,542,249 B1 | 4/2003 | Kofman et al. | 356/601 |
| 6,603,103 B1 | 8/2003 | Ulrich et al. | 250/205 |
| 6,750,975 B2 | 6/2004 | Takeda et al. | 356/604 |

(Continued)

FOREIGN PATENT DOCUMENTS

DE   40 07 502 A1   9/1991

(Continued)

OTHER PUBLICATIONS

International Preliminary Report on Patentability for International Application No. PCT/EP2008/065627, Nov. 27, 2009 (and English translation thereof).

*Primary Examiner* — Vikkram Bali
*Assistant Examiner* — Nancy Bitar
(74) *Attorney, Agent, or Firm* — Fitzpatrick, Cella, Harper & Scinto (57) ABSTRACT

A method for optically measuring an object by means of an optical recording apparatus includes a triangulation method. A first shutter means is used to produce a first pattern and to project the first pattern as a first projection beam onto the object to be measured. At least one further shutter means is used to produce a further pattern and to project the further pattern as a further projection beam onto the object to be measured. The first pattern and the further pattern are passed back from the object as observation beams and are recorded by at least one recording means in order to obtain a three-dimensional data record of the object. The projected first pattern and the further pattern are recorded at the same time in at least one triangulation recording using the at least one recording means.

23 Claims, 3 Drawing Sheets

U.S. PATENT DOCUMENTS

| | | | |
|---|---|---|---|
| 7,184,150 B2 * | 2/2007 | Quadling et al. | 356/602 |
| 2003/0223083 A1 | 12/2003 | Geng | 356/603 |
| 2004/0105580 A1 | 6/2004 | Hager et al. | 382/154 |
| 2004/0151365 A1 | 8/2004 | An Chang et al. | 382/154 |
| 2009/0238499 A1 | 9/2009 | Steele | 383/200 |

FOREIGN PATENT DOCUMENTS

| | | |
|---|---|---|
| DE | 42 06 836 A1 | 9/1993 |
| DE | 196 34 254 A1 | 3/1997 |
| DE | 196 37 682 A1 | 3/1998 |
| DE | 197 47 061 A1 | 5/1999 |
| EP | 0 160 797 B1 | 1/1989 |
| EP | 0 923 705 B1 | 6/1999 |
| WO | WO 93/03579 | 2/1993 |
| WO | WO 2004/085956 A2 | 10/2004 |
| WO | WO 2007/061632 A2 | 5/2007 |
| WO | WO 2007/061632 A3 | 5/2007 |

* cited by examiner

METHOD FOR OPTICAL MEASUREMENT OF OBJECTS USING A TRIANGULATION METHOD

CROSS REFERENCE TO RELATED APPLICATIONS

The present application is a continuation of International Application No. PCT/EP2008/065627, filed Nov. 14, 2008, which claims priority to German Patent Application No. 10 2007 054 907.7, filed Nov. 15, 2007. The entire disclosure of each prior application is incorporated by reference herein.

BACKGROUND OF THE INVENTION

1. Field of the Invention

The invention relates to a method for optical measurement of the three dimensional geometry of objects and is concerned with the task of 3D scanning when there is relative movement between the camera and the object when being scanned, particularly for dental purposes.

2. Prior Art

Digital design data for the computer-assisted production of dental prosthetic items without having to create the usual impression can be acquired by optically scanning one or more teeth in a patient's mouth.

For such scanning, use is frequently made of measuring methods based on the principle of triangulation. Phase-shifting triangulation is disclosed in EP 0 160 797, in which a three-dimensional data set is acquired from a sequence of images of a pattern which is shifted in position from image to image.

With prior triangulation methods, a single straight stripe of light is projected by a projector onto the object being scanned and the projected image is captured by a camera at a parallax angle in the monitoring direction so as to produce an image.

Depending on the surface structure of the object, the light stripe appears no longer to be straight, but curved and offset with respect to its straight form. The surface structure of the object being scanned may then be concluded from the position and shape of the light stripe.

By moving the light stripe transversely to the direction of orientation of the light stripe, the entire object can be scanned to produce images. The altitude data of the scanned object acquired from each individual image can be stored in the form of a two-dimensional pattern in the memory of a computer, which corresponds to a projection of the altitude information of the surface of the scanned object onto a base surface as the reference surface. Following the scanning operation there is obtained a digital, three-dimensional data model of the scanned object, which can be displayed, for example, on a screen as a video still.

A method for the production of a three-dimensional image of an object being scanned is disclosed in WO 2004/085956 A2, a procedure which improves the above-described scanning method in that the surface structure of the scanned object is measured completely during an exposure Pi.

The light stripe can be produced, for example, by the rapid movement of a laser beam throughout the period of image creation such that the light stripe is actually composed of points of light. During an exposure Pi, the pinpoint light beam of a laser is directed over the object being scanned, along a 2-dimensional pattern for the light stripes, in which at least some of the light stripes are substantially parallel to each other, i.e. extend in a direction R1. Space is provided between the light stripes.

During an exposure, the altitude data of the object being scanned are collected along a plurality of parallel, spaced light stripes or sections thereof.

Thus the image obtained already provides the altitude data of the object being scanned in a first group of a plurality of spaced lines of the two-dimensional pattern of the yet to be produced three-dimensional data set.

The independent altitude data acquired from the individual images are merged in the two above-described procedures involving stripe projection which is quasi-static during each exposure, involving one stripe per exposure or a plurality of discrete stripes per exposure, as is known from WO 2004/085956 A2, thus forming an overall image describing or containing all of the 3D data of the object being scanned.

The disadvantage of the described measuring methods involving triangulation is that, due to the fact that a sequence of individual images is created and then a set of at least two images is combined to form an overall image, any camera-shake of the recording apparatus relative to the object between the individual can result in image defects. The position of the recording apparatus relative to the object thus has to remain unchanged when creating a set of images, and can be changed only in the next step for creating a subsequent set of images. An on-the-fly measurement of the object, in which several complete images of the object are created in short periods of time, is thus impossible. The present problem is to provide a method for optical measurement of objects by means of triangulation, particularly for dental purposes, which method is to be capable of allowing on-the-fly measurement.

SUMMARY OF THE INVENTION

This object is achieved by the following features of the invention.

According to the invention, a method is provided for optical measurement of the three-dimensional geometry of an object by means of triangulation with the aid of an optical recording apparatus. The recording apparatus comprises at least one light source, at least one diaphragm unit for creating structured patterns and at least one recording unit. With the aid of the first diaphragm unit, a first pattern is created and projected in the form of a first projected beam onto the object being scanned, an additional pattern being created by means of at least one additional diaphragm unit and projected in the form of an additional projected beam onto the object being scanned, the first pattern and the additional pattern being back-projected from the object in the form of monitoring beams which are imaged by the at least one recording unit in order to obtain a 3D data set of the object. The projected first pattern and the additional pattern are imaged simultaneously to form at least one triangulation image using the at least one recording apparatus.

The triangulation method used in the present invention is based on the following principle:

A specific measurement point on an object being scanned is illuminated from one direction by a projected beam and monitored from another direction by a sensor.

Thus there are two angles between the baseline (connecting the light source and the sensor) and the projected beam and monitoring beam respectively. Knowing the length of the baseline, it is possible to determine the coordinates of the measured point with respect to the coordinate system of the recording apparatus comprising the light source and the sensor.

Advantageously, the present invention utilizes the stripe projection method, in which a pattern of parallel stripes is projected onto the object being scanned, by which means a plurality of measurement points can be scanned simultaneously.

In order to determine the coordinates of the measurement point, one projection coordinate must be known that assigns a measurement point to an image coordinate on the sensor. The measurement points must be assigned to the respective light stripes.

Such assignment can be effected by counting the stripes by evaluating the sequence of brightness values registered on the sensor, so as to determine the number of the respective stripe.

This assignment can alternatively be accomplished using a binary code method (a gray-scale code, for example), in which each stripe contains a binary sequence of brightness values representing the number of the stripe. By reading and interpreting this code, it is possible to determine the number of each stripe.

A higher degree of precision for the assignment of projection coordinates can be obtained using the so-called phase shift method, in which the 3D data of the object being scanned can only be generated after reading at least four individual phase-shifted images. The brightness values of the individual stripes have a sinusoidal shape, the phase of which differs in the patterns of the individual triangulation image. For each measurement point, there arise at least four brightness values from the individual triangulation images, from which the phase position of this measurement point can be calculated by a mathematical procedure, and then the position of the measurement point on the coordinate axis normal to the stripes can be determined from the phase position.

The advantage of assigning by counting and using the binary code method resides in the fact that the 3D data for the area of measurement illuminated by the pattern can be generated immediately after each individual triangulation recording.

The advantage of the phase shift method is that, unlike assigning by counting or the binary code method, a measurement point is not assigned to a specific stripe and thus to a discrete coordinate, but a non-discrete coordinate of the measurement point is determined that can also be located between two stripes. Consequently, a higher degree of precision is achieved.

The pattern can be composed of a single stripe or of a plurality of parallel stripes. The optical recording apparatus can be a dental camera or some other optical assembly.

The recording apparatus can comprise at least one light source that can be a conventional illuminant, a colored LED, a white LED, or a laser. Both monochromatic and polychromatic light is well suited for the triangulation method. The light sources for the individual patterns can differ in terms of their wavelength so that they can be distinguished from each other in a common triangulation image.

The recording apparatus can be a plurality of diaphragm units for creating structured patterns, each diaphragm unit being able to create one pattern. The diaphragm unit can be an optical grid comprising structured slits. The structured slits can include parallel stripes.

The object being scanned can be any three-dimensional object, the present method being particularly well suited for scanning teeth.

The light from the light source passes through the diaphragm unit so that a structured pattern develops that is projected onto the object in the form of a projected beam. The light of the projected pattern is then back-projected from the object as a monitoring beam and is imaged by at least one recording unit in at least one triangulation image concurrently with the other patterns. The recording unit can be an optical sensor or in particular, a CCD sensor. The projected patterns can be imaged from different monitoring directions to give a plurality of triangulation images.

The different patterns in the triangulation image are separately analyzed, and 3D data of the regions covered by the patterns are generated. Then the individual 3D data of the patterns are combined to form a 3D data set of the object.

One advantage of the method of the invention is that the individual patterns projected onto the object are imaged simultaneously. In traditional methods, the individual patterns are imaged as a sequence of individual images. As a result, the recording apparatus can suffer camera-shake between exposures, and the position of the recording apparatus can thus change relatively to the object. This defect caused by camera-shake of the recording apparatus can then be corrected by complicated computer-assisted techniques. However, there is no risk of camera-shake in the present method on account of the simultaneous recording of patterns.

A further advantage of the present method is that it makes on-the-fly measurement possible. In conventional methods, a specific area of measurement could be scanned to give a sequence of triangulation images involving shifted patterns, and the position of the recording apparatus had to remain unchanged, as far as possible, in relation to the object when recording the set of images. A new area of measurement could be imaged to provide a new set of triangulation images only in a subsequent step. By contrast, in the present method, the patterns of a set are imaged simultaneously and the area of measurement is thus scanned at the same point in time. In the next step, the recording apparatus can be moved relatively to the object and an adjacent area of measurement can be imaged simultaneously following a predetermined period of time. A series of triangulation images can thus be created by on-the-fly measurement, and these triangulation images can be combined to form an overall 3D image of the object using computer-assisted methods.

Advantageously, the first pattern and the additional pattern can be projected onto the object in the form of beams projected in a common direction of projection.

The patterns can be created with the aid of a plurality of diaphragm units and the projected beams can be deflected such that the patterns are projected onto the object in a common direction of projection. As a result, the recording apparatus can be provided with a more compact design and an area of measurement on the object can be imaged entirely from one common direction of projection.

Advantageously, the monitoring beams of the patterns can be imaged from at least two monitoring directions, there being an angle of offset between the first monitoring direction and the other monitoring direction.

As a result, the projected patterns can be imaged simultaneously from several monitoring directions. The angle between the monitoring directions should preferably be between 20° and 90°. Attention is drawn to the fact that, for proper functioning of the triangulation method, the stripes of the pattern should have an angle of at least 10° with respect to the plane of triangulation as defined by the direction of projection and the monitoring direction.

Advantageously, the monitoring beams of the patterns can be imaged by means of a plurality of recording apparatuses to give a plurality of individual triangulation images created from different monitoring directions.

The simultaneously projected patterns are consequently imaged in at least two triangulation images by at least two discrete recording units. By combining these triangulation images imaged from different monitoring directions, a higher precision of measurement is achieved and, in particular, concave and convex areas of measurement of the object can be scanned in their entirety.

Advantageously, the projected beams of the patterns can be projected onto the object from at least two different directions of projection. The monitoring beams of the patterns are imaged from a single monitoring direction, the first direction of projection showing an angular offset relative to the other direction of projection.

As a result, the patterns are simultaneously projected onto the object from different directions of projection so that the patterns cover the object from different directions and a more complete image of the object is thus generated. Furthermore, the projected beams of the different patterns need not be deflected relatively to a common direction of projection.

Advantageously, the individual patterns can be coded for distinguishing them from each other and for identifying them in the at least one triangulation image.

The individual patterns in the triangulation image can thus be identified in the case of one recording unit from one monitoring direction or from a plurality of triangulation images in the case of a plurality of recording units from different monitoring directions and analyzed separately.

Advantageously, the individual patterns can be color-coded in that the first pattern has a first wavelength and the further pattern has a wavelength deviating therefrom, at least one color sensor being present as recording unit, the measurement range of which covers all wavelengths of the patterns and makes separate analysis of the differently colored patterns possible.

The different patterns can thus be scanned simultaneously by at least one color sensor, and distinguished from each other on the basis of their wavelength for the purpose of separate analysis. The light for the patterns can be emitted from light sources of different wavelengths. The light used can be monochromatic light having different wavelengths and polychromatic light showing different spectra.

Advantageously, the individual patterns can be provided with a binary gray-scale code, and the individual patterns in the at least one triangulation image can be identified on the basis of this gray-scale code.

As a result, the different patterns in the common triangulation image can be identified and analyzed separately. The binary gray-scale code contains a binary sequence of brightness values, from which it is possible to decode the number of the pattern.

Advantageously, the projected beams of the patterns can be projected onto the object from at least two different directions of projection, the monitoring beams of the patterns being imaged from at least two different monitoring directions.

As a result, the patterns are projected onto the object from a plurality of directions of projection and the area of measurement of the object is scanned from a plurality of monitoring directions. It is thus possible to generate a plurality of triangulation images from different monitoring directions, which images can be superimposed in order to obtain a more complete 3D model.

Advantageously, the first direction of projection of the first pattern can enclose an angle of more than 10° with the further direction of projection of the further pattern.

As a result, the directions of projection differ from each other by an angle of at least 10° so that the light sources and the diaphragm units for creating the patterns can be juxtaposed.

Advantageously, the first monitoring direction can enclose an angle of more than 10° with the further monitoring direction. As a result, the recording units such as CCD sensors can be juxtaposed in the monitoring directions.

Advantageously, the evaluation of the at least one triangulation image can be carried out by a stripe projection method on the basis of the triangulation method.

In the stripe projection method, the pattern is composed of a plurality of parallel stripes, the stripes being preferably oriented at right angles to the plane of triangulation. The coordinates of the measurement point are determined by means of the methods described above involving counting the stripes, the binary code method, or the phase shift method.

Advantageously, apart from the triangulation images, supplementary images of the object can be imaged from different monitoring directions based on the principle of photogrammetry, and then implemented for evaluation of the triangulation images.

Photogrammetry involves a group of measuring methods to determine the spatial position and three-dimensional shape of an object from photographic images of the object taken from different directions. Usually, high-resolution digital cameras are used for creation of the photographic images. Photogrammetry is a computer-assisted technique in which 3D coordinates of object points are determined from the individual photographic images with the aid of pattern recognition and central projection. The supplementary images are thus imaged from different directions and an supplementary photogrammetric 3D data set of the object is generated by way of photogrammetry. The photogrammetric 3D data set is superimposed on the first 3D data set generated using the triangulation method, in order to increase the precision of measurement.

Advantageously, it is possible to carry out both an evaluation of the triangulation images on the basis of the principle of stripe projection and an evaluation of the supplementary images on the basis of the principle of photogrammetry with the aid of an evaluating unit.

The evaluation of the triangulation images on the basis of the principle of stripe projection and of the supplementary images on the basis of the principle of photogrammetry can be effected by means of an evaluating unit such as a computer.

Advantageously, the recording units can consist of CCD sensors.

Advantageously, the evaluating unit can use the individual triangulation images to generate 3D data of each region of the object scanned and combine these 3D data to form an overall 3D data set of the object.

The evaluating unit can be a computer. The measuring setup of the optical recording apparatus is known, and in particular, the spatial directions of projection and the monitoring directions and the length of the baseline between the recording units and the light sources are known, so that the 3D data can be computed from the projection of a pattern by means of the evaluating unit using the triangulation method. Taking the angles of the directions of projection and of the monitoring directions of the individual patterns with respect to each other, it is possible to combine the 3D data to form a common 3D data set.

Advantageously, a display unit can be present that graphically displays the entire 3D data set of the object as a 3D model.

The display unit can be a computer monitor capable of displaying the entire 3D data set as a three-dimensional model.

Advantageously, when using the stripe projection method, the individual patterns can be composed of a plurality of parallel stripes.

Advantageously, the at least two triangulation images can be analyzed from different monitoring directions, the triangulation images being superimposed with reference to regions that match each other. The ICP method or the topology matching method is used as the analysis technique for localizing the regions that match each other.

The patterns projected onto the object are imaged from different monitoring directions by spaced recording units such as CCD sensors. The position of the recording units relative to each other and their monitoring directions are known so that the positional relationship between the triangulation images is computed therefrom and these triangulation images are combined to form an overall 3D data set of the object.

Alternatively, it is possible to determine those regions of the patterns that match each other in the different triangulation images and to superimpose the triangulation images with reference to these matching regions. The ICP method or the topology matching method can be used as analysis techniques.

The so-called ICP (Iterative Closest Point) method is used for the alignment of 3D data that are similar in form in at least some regions.

The topology matching method is a method used in image processing and uses MRGs (Multiresolutional Reeb Graphs) for the comparison of different topologies. MRGs are especially well suited as search criteria for similar 3D data sets. The computation of such similarity takes place quickly and efficiently with this method, since it necessitates no computation of a change in position or of any rotation.

Advantageously, the 3D data can be generated exclusively by analyzing the patterns of each triangulation image, the individual stripes being identified by counting the stripes or by using a binary code method.

In the stripe projection method, the coordinates of a measurement point in the triangulation images are determined. For this purpose, each stripe that has covered a measurement point is assigned thereto. Such assignment can be effected using the method of counting the stripes, as described above, involving the evaluation of the sequence of brightness values registered on the sensor so as to determine the number of each individual stripe.

This assignment can alternatively be accomplished using the binary code method (Gray code, for example), described above, in which each stripe contains a binary sequence of brightness values representing the number of the stripe. It is possible to determine the number of each stripe by evaluating this binary code.

Advantageously, the 3D data of an individual triangulation image can be generated by analyzing at least four differently phased patterns in the at least one triangulation image, a phase shift method being used to determine the coordinates of a measurement point.

The phase shift method described above provides a higher degree of precision for the assignment of projection coordinates. In the phase shift method, the 3D data of the object can only be generated after evaluating at least four individual images of phase-shifted patterns. The phase-shifted patterns are simultaneously projected onto the object and imaged to give at least one triangulation image. The individual patterns are then analyzed separately. The phase position of the measurement points and then their coordinates are determined by means of the evaluating unit.

Advantageously, projecting means can be provided for concurrent projection of at least two patterns onto the object. These projecting means can be a diaphragm unit for creating the patterns and deflecting means for changing the direction of projection.

Advantageously, in a first step, a first group of patterns can be simultaneously imaged in at least a first triangulation image using the at least one recording units, and in a further step, a further group of patterns can be simultaneously imaged after a predetermined period of time to give at least one further triangulation image with the aid of further recording units, the position of the recording apparatus being changed relatively to the object being scanned during this period of time.

Consequently, on-the-fly measurement is carried out. A first group of patterns is simultaneously imaged to give a first triangulation image. The recording apparatus is moved relatively to the object and a further group of patterns is simultaneously imaged to give a further triangulation image. A sequence of triangulation images is thus created from different directions in a predetermined period of time.

Advantageously, a first 3D data set of the object can be acquired from the first group of patterns in the first triangulation image, and a further 3D data set of the object can be acquired from the further group of patterns in the further triangulation image. The first 3D data set and the further 3D data set are then combined to form a common 3D image of the object.

BRIEF DESCRIPTION OF THE DRAWINGS

Exemplary embodiments of the invention are illustrated in the drawings, in which.

EMBODIMENTS OF THE INVENTION

Figure 1:
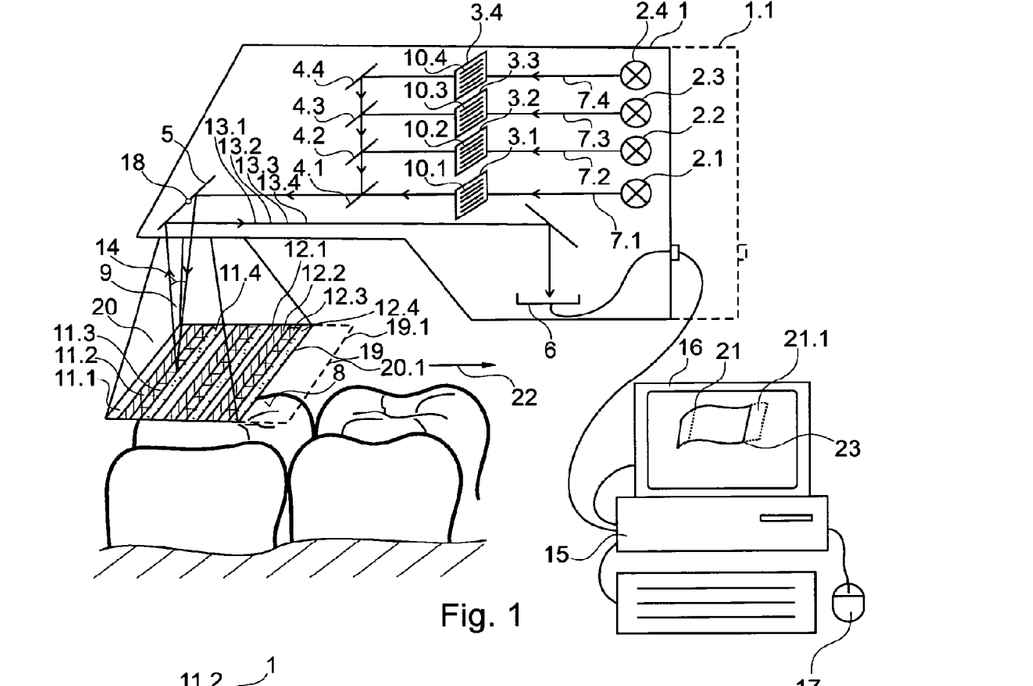
FIG. 1 is a sketch illustrating the method of the invention, showing a dental intraoral camera as a recording apparatus for scanning purposes, which recording apparatus includes a projector and has one monitoring direction.

FIG. 1 is a sketch for illustration of the method of the invention. A dental intraoral camera is used as a recording apparatus 1, which dental intraoral camera comprises four light sources 2.1, 2.2, 2.3, 2.4, four diaphragm units 3.1, 3.2, 3.3, 3.4, four deflecting means 4.1, 4.2, 4.3, 4.4, a mirror 5 and a CCD sensor 6 as the recording units. The light sources 2.1, 2.2, 2.3, 2.4 emit projected beams 7.1, 7.2, 7.3, 7.4 that pass through the diaphragm units formed as grids 3.1, 3.2, 3.3, 3.4 and are deflected by the deflecting means 4.1, 4.2, 4.3, 4.4 to the mirror 5 and directed by the mirror 5 onto an object 8, namely the surface of a tooth. The deflecting means 4.2, 4.3, 4.4 completely deflect the projected beams 7.2, 7.3, 7.4, while the deflecting means 4.1 is semi-transparent and therefore allows the passage of the projection beam 7.1 therethrough and the partial deflection of the deflected projected beams 7.2, 7.3 and 7.4 to the mirror 5. The diaphragm units formed as optical grids 3.1, 3.2, 3.3, 3.4 comprise slits 10.1, 10.2, 10.3, 10.4 that are perpendicular to the plane of triangulation 9 so that structured patterns 11.1, 11.2, 11.3, 11.4 are created and projected onto the object 8 as light passes through the grids 3.1, 3.2, 3.3, 3.4. The patterns 11.1, 11.2, 11.3, 11.4 are in the form of parallel stripes 12.1, 12.2, 12.3, 12.4. For purposes of illustration, the parallel stripes 12.1 of the first pattern 11.1 are drawn without hatching, the parallel stripes 12.2 of the second pattern 11.2 are drawn with single hatching, the parallel stripes 12.3 of the third pattern 11.3 are drawn with cross-hatching and the parallel stripes 12.4 of the fourth pattern 11.4 are dotted. The four structured patterns 11.1, 11.2, 11.3, 11.4 are shown only diagrammatically and do not depict the actual projection of the light stripes 12.1, 12.2, 12.3, 12.4 on the object 8 being scanned, but merely illustrate the arrangement of the patterns 11.1, 11.2, 11.3, 11.4 in relation to each other and also the direction of projection. The projected beams 7.1, 7.2, 7.3, 7.4 are reflected from the surface of the object 8 being scanned and are back-projected as monitoring beams 13.1, 13.2, 13.3, 13.4 in a common optical path and directed to the CCD sensor 6 and detected thereby. The plane of triangulation 9 is defined by the projected beams 7.1, 7.2, 7.3, 7.4 and the monitoring beams 13.1, 13.2, 13.3, 13.4. The projected beams 7.1, 7.2, 7.3, 7.4 enclose with the back-projected monitoring beams 13.1, 13.2, 13.3, 13.4 a so-called triangulation angle 14. The image data acquired by the CCD sensor 6 are sent to a computer that functions as an evaluating unit 15, which has a monitor as a display unit 16 and a keyboard and mouse functioning as inputting units 17.

In the present method, the mirror 5 is not adjustable and the patterns 11.1, 11.2, 11.3, 11.4 are projected simultaneously onto the object 8, the individual patterns 11.1, 11.2, 11.3, 11.4 are shifted toward each other by a stripe's width and the surface of the object 8 being scanned within a rectangular area of measurement 19 is covered without showing any gaps. The monitoring beams 13.1, 13.2, 13.3, 13.4 of the individual patterns 11.1, 11.2, 11.3, 11.4 are simultaneously imaged by the CCD sensor to give a first common triangulation image 20. The individual patterns 11.1, 11.2, 11.3, 11.4 are coded for distinguishing them from each other in that the first pattern 11.1 has a first wavelength, the second pattern 11.2 a second wavelength, the third pattern 11.3 a third wavelength, and the fourth pattern 11.4 a fourth wavelength. The CCD sensor is configured such that its range of measurement includes all of the wavelengths of the patterns 11.1, 11.2, 11.3, 11.4 and allows for separate analysis thereof. The image data of the first triangulation image 20 are sent to the evaluating unit 15, where the projections of the individual patterns 11.1, 11.2, 11.3, 11.4 are analyzed separately and 3D data of the detected regions are computed by the triangulation method. When computing the 3D data by the triangulation method, the coordinates of the measurement points relative to the coordinate system of the recording apparatus are determined from the known length of a baseline and the known angles between the projection beam and the baseline, and the monitoring beam and the baseline, which baseline joins the light sources 2.1, 2.2, 2.3, 2.4 and the CCD sensor 6 when the projection beam and the monitoring beam extend in a straight path.

The 3D data of the individual patterns 11.1, 11.2, 11.3, 11.4 acquired by means of the evaluating unit 15 are combined to form an overall 3D data set, which is displayed on the display unit 16 as a 3D model 21 of the surface of the object 8 scanned within the area of measurement 19.

In traditional triangulation procedures, the projections of the different patterns are imaged consecutively in a timed sequence in multiple individual images. Camera-shake between the images causes defects in the image. However, such defects in the image are not possible when using the present method since the patterns 11.1, 11.2, 11.3, 11.4 are imaged simultaneously in a common plane of triangulation. This makes on-the-fly measurement possible, in which, after the first triangulation image 20 has been created, the recording apparatus 1 is moved in the direction 22 to a second position 1.1 and an adjacent region of the surface of the object 8 within an area of measurement 19.1 that is offset in the direction 22 is scanned to form a second triangulation image 20.1. A first 3D data set is acquired from the first triangulation image and a second 3D data set is acquired from the second triangulation image 20.1. The second 3D data set is likewise displayed on the display device 16 as a 3D model 21.1 represented by hatching. The first 3D data set 21 is combined with the second 3D data set 21.1 to form a common 3D image 23 displayed by the display device 16. In the on-the-fly measurement procedure, triangulation images are made at predetermined points in time until the entire object 8 has been scanned.

Figure 2A:
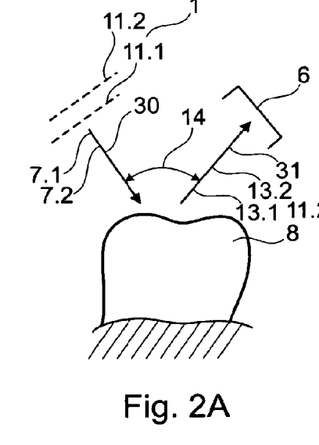
FIG. 2A is a diagrammatic sketch of the recording apparatus shown in FIG. 1, as a side view showing a common direction of projection for two patterns and one monitoring direction.

FIG. 2A is a diagrammatic sketch of the recording apparatus shown in FIG. 1, and the projected beams 7.1, 7.2 of the patterns 11.1 and 11.2 are projected along a common direction of projection 30 onto the object 8, and the monitoring beams 13.1 and 13.2 are imaged by the CCD sensor 6 in a common monitoring direction 31. The patterns 11.1 and 11.2 are created by the diaphragm unit 10.1 and 10.2, and deflected with the aid of the deflecting means 4.1, 4.2 such that the patterns are projected along a common direction of projection 30 onto the object 8. The advantage of this is that the recording apparatus 1 can be provided with a more compact design and the area of measurement 19 including patterns 11.1 and 11.2 can be scanned completely in a common direction of projection. Only two patterns are illustrated for the purpose of diagrammatic simplification. However, the number of patterns can be increased depending on the desired resolution.

Figure 2B:
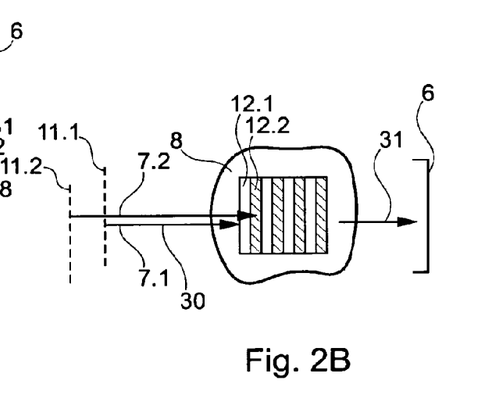
FIG. 2B is a diagrammatic sketch of the recording apparatus shown in FIG. 1, as a top view showing a common direction of projection for two patterns and one monitoring direction.

FIG. 2B shows diagrammatically the arrangement shown in FIG. 2A as a top view. The patterns 11.1 and 11.2 are projected onto the object 8 and they form projected images in the form of parallel stripes 12.1 and 12.2. The patterns are then imaged by means of the CCD sensor 6 in the common monitoring direction 31 to give a common triangulation image 20 as shown in FIG. 1.

Figure 3:
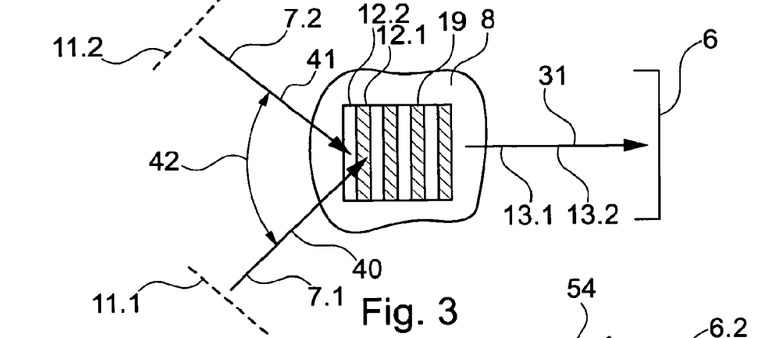
FIG. 3 is a diagrammatic sketch as a top view showing two different directions of projection and one monitoring direction.

FIG. 3 shows diagrammatically the arrangement as a top view. The patterns 11.1 and 11.2 are projected in the form of projected beams 7.1 and 7.2 along different directions of projection 40 and 41 onto the object 8 within the area of measurement 19 as parallel stripes 12.1 and 12.2. The monitoring beams 13.1 and 13.2 of the projected parallel stripes 12.1 and 12.2 are scanned along a common monitoring direction 31 by means of the CCD sensor 6. The first direction of projection 40 encloses an angle 42 with the second direction of projection 41. As a result, the object 8 is scanned simultaneously from different directions of projection 40 and 41 and thus a more complete image of the object is generated. The projected beams 7.1 and 7.2 need not therefore be deflected in a complicated manner as in FIGS. 1, 2, and 2B to form a common direction of projection 30.

Figure 4:
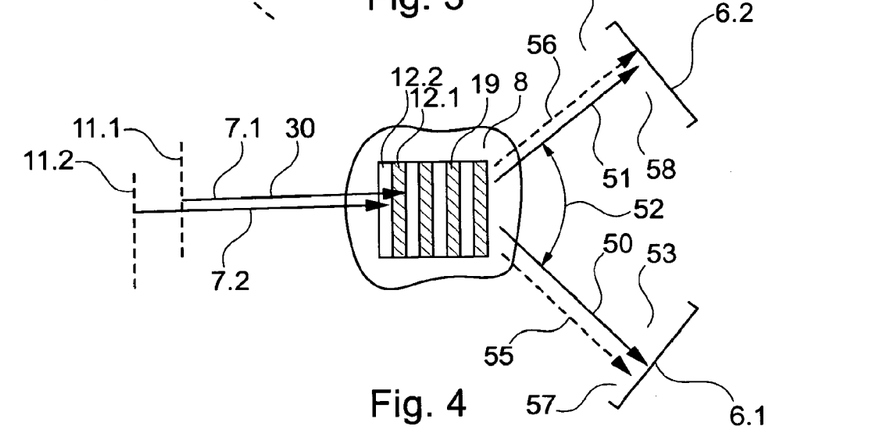
FIG. 4 is a diagrammatic sketch as a top view showing one direction of projection and two different monitoring directions.

FIG. 4 is a diagrammatic illustration of an supplementary embodiment as a top view, in which the projected beams 7.1, 7.2 of the patterns 11.1, 11.2 are projected along a common direction of projection 30 onto the object 8 within an area of measurement 19 in the form of parallel stripes 12.1, 12.2, and the parallel stripes 12.1, 12.2 are scanned with the aid of a first CCD sensor 6.1 in a first monitoring direction 50 and by means of a second CCD sensor 6.2 in a second monitoring direction 51. The first monitoring direction 50 encloses an angle 52 with the second monitoring direction 51. The angle 52 can be larger than 10°, so that the CCD sensors 6.1 and 6.2 can be juxtaposed. The advantage of this embodiment is that the parallel stripes 12.1 and 12.2 are scanned simultaneously from two different monitoring directions 50 and 51, and can be produced, particularly in the case of an uneven surface of the object 8, by superimposition of a triangulation image 53 created by means of the first CCD sensor 6.1 and a second triangulation image 54 created by means of a second CCD sensor 6.2.

In addition to the triangulation images 53 and 54, supplementary images 57 and 58 are created from the monitoring directions 55 and 56 on the basis of the principle of photogrammetry. In doing so, the same CCD sensors 6.1 and 6.2 are used, these being capable of creating photographic images of the object 8 in addition to the stripe pattern for the triangulation images. The resolution of the CCD sensors 6.1 and 6.2 must be suitable for creating photographic images. The supplementary photographic images 57, 58 of the object from the two monitoring directions 55, 56 are evaluated by the evaluating unit 15 shown in FIG. 1 using computer-assisted methods such as pattern recognition and central projection, and a photogrammetric 3D data set of the object 8 is acquired. The photogrammetric 3D data set generated from the supplementary images 57 and 58 is superimposed by the first 3D data set generated according to the triangulation method, thereby enhancing the precision of the measurement.

Figure 5:
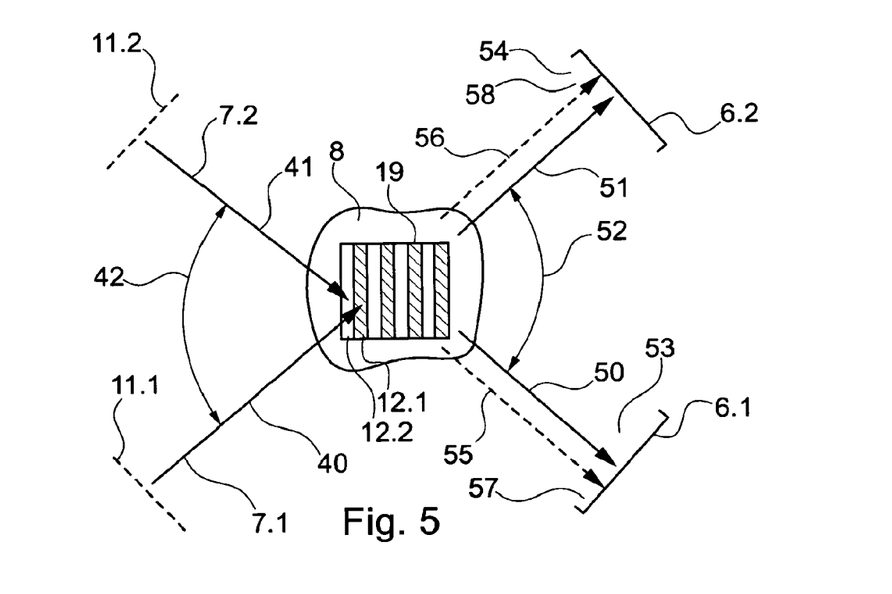
FIG. 5 is a diagrammatic sketch as a top view showing two directions of projection and two monitoring directions.

FIG. 5 shows diagrammatically the architecture of an supplementary embodiment as a top view, in which the two projected beams 7.1 and 7.2 of the patterns 11.1, 11.2 are projected onto the object 8 within the area of measurement 19 along different directions of projection 40, 41, and the projected parallel stripes 12.1, 12.2 are then scanned along a first monitoring direction 50 and a second monitoring direction 51 by means of the CCD sensors 6.1 and 6.2. The first direction of projection 40 encloses an angle 42 with the second direction of projection 41, and the first monitoring direction 50 encloses an angle 52 with the second monitoring direction 51.

In the embodiments shown in FIG. 1, FIG. 2A, FIG. 2B, and FIG. 4, the projected beams 7.1, 7.2 are projected onto the object 8 along a common direction of projection. By contrast, in the embodiment shown in FIG. 3 and FIG. 5, the projected beams 7.1, 7.2 are projected onto the object 8 along different directions of projection 40, 41 so that the distance of the recording apparatus 1 and thus of the diaphragm units 3.1, 3.2 from the surface of the object 8 influences the arrangement of the parallel stripes 12.1 and 12.2 with respect to each other. The diaphragm units 3.1, 3.2 and the other optical elements of the recording apparatus 1 must be arranged such that for a given scanning distance between the recording apparatus and the surface of the object 8, the stripes 12.1, 12.2 do not overlap, but instead provided gapless coverage of the surface of the object 8 within the area of measurement 19, as shown. This technical problem does not occur in the embodiments shown in FIG. 1, FIG. 2A, FIG. 2B, and FIG. 4 involving a single direction of projection 30, since the position of the parallel stripes 12.1 relative to the parallel stripes 12.2 does not vary with the distance between the recording apparatus 1 and the surface of the object 8.

In addition to the two triangulation images 53 and 54, supplementary photographic images 57, 58 are created, from which a photogrammetric 3D data set is generated, as shown in FIG. 4, which is superimposed by the first 3D data set 21 shown in FIG. 1 for improving the precision of measurement.

Figure 6:
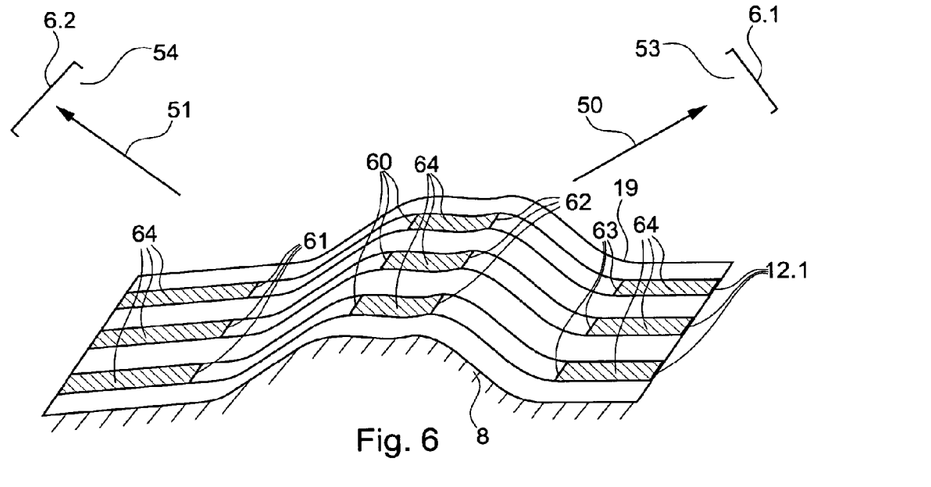
FIG. 6 is a sketch of a pattern projected onto an uneven object showing two different monitoring directions for illustrating the superimposition of triangulation images with respect to matching regions.

FIG. 6 is a sketch of the patterns 11.1 and 11.2 projected onto an uneven surface of the object 8 within the area of measurement 19. For purposes of illustration, only the parallel stripes 12.1 of the first pattern are shown. The stripes 12.1 of the first pattern 11.1 are scanned, as in the embodiment shown in FIG. 4 and FIG. 5, from a first monitoring direction 50 by means of the first CCD sensor 6.1 and from a second monitoring direction 51 by means of a second CCD sensor 6.2. The first triangulation image 53 is generated from the image data produced by the sensor 6.1, and a second triangulation image 54 is generated from the image data produced by the second CCD sensor 6.2. The two triangulation images 53 and 54 are brought into register with the aid of the evaluating unit 15 shown in FIG. 1 and are combined to form a common 3D image 23 as shown in FIG. 1. The positional relationship between the first triangulation image 53 and the second triangulation image 54 can be computed on the basis of the position of the recording apparatus 6.1, 6.2 relative to each other and their monitoring directions 50, 51.

Alternatively, the triangulation images 53 and 54 can be superimposed on the basis of those regions of the projected patterns 11.1 and 11.2 that match each other. In the first monitoring direction 50, those regions of the parallel stripes 12.1 that are disposed between the positions 60 and 61 are not visible due to the geometry of the surface of the object 8. In the second monitoring direction 51, those regions of the parallel stripes 12.1 that are disposed between the positions 62 and 63 are not visible. The two triangulation images 53 and 54 must thus be superimposed and combined in order to achieve a complete image of the surface of the object 8. The first triangulation image 53 and the second triangulation image 54 include regions 64 that match each other and are illustrated by hatching. These regions 64 in the triangulation images 53 and 54 that match each other can be determined using computer-assisted analysis techniques, and the triangulation images 53 and 54 can be superimposed with reference to these corresponding regions 64. The so-called ICP method and the topology matching method are suitable as computer-assisted analysis techniques.

Figure 7:
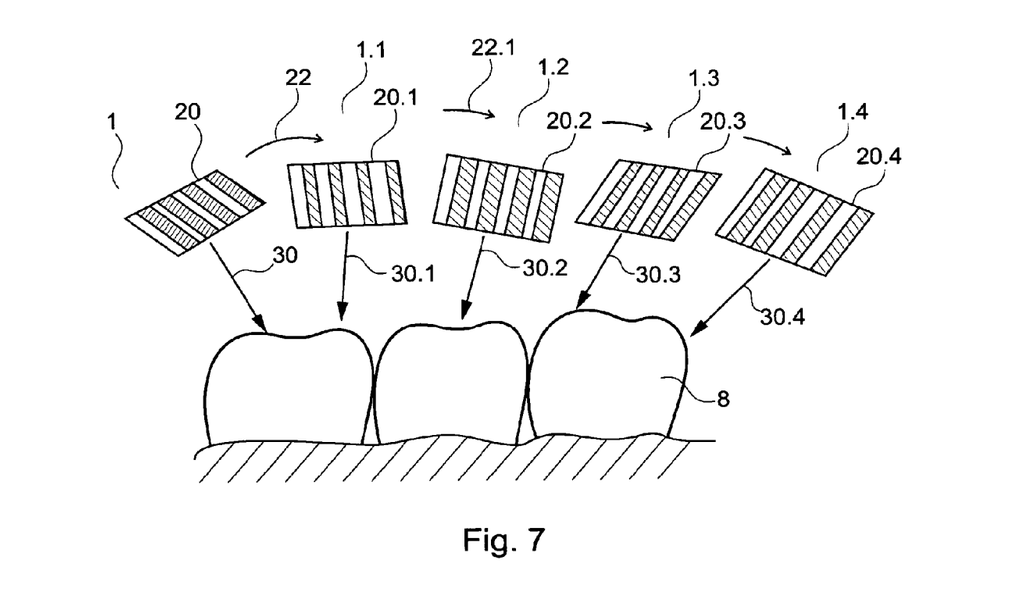
FIG. 7 is a sketch for illustrating on-the-fly measurement using triangulation images created from different directions.

FIG. 7 is a diagrammatic illustration of an on-the-fly scan. In the case illustrated, the object 8 to be scanned is a row of teeth consisting of three teeth. A first triangulation image 20 is created from a first direction of projection 30, and the recording apparatus 1 is turned in the direction 22 to a second position 1.1, as shown in FIG. 1, this direction 22 having an arcuate form. After a predetermined period of time, a second triangulation image 20.1 is created in a second direction of projection 30.1 from the second position 1.1 of the recording apparatus, and the recording apparatus is turned to a third position 1.2. A third triangulation image 20.2 is created in a third direction of projection 30.2 and the recording apparatus is turned in a direction 22.2 to a fourth position 1.3, and a fourth triangulation image 20.3 of the object 8 is created in a fourth direction of projection 30.3. Finally, the recording apparatus is turned to a fifth position 1.4. and a fifth triangulation image 20.4 of the object 8 is created in a fifth direction of projection 30.4. The 3D data sets acquired from the triangulation images 20, 20.1, 20.2, 20.3, 20.4, as described above with reference to FIG. 1, are combined to form a common 3D image 23 that contains all of the 3D data of the entire object 8 being scanned. The on-the-fly measurement can be continued until the entire object 8 has been scanned. The triangulation images 20, 20.1, 20.2, 20.3, 20.4 are combined on the basis of the regions that match each other using a computer-assisted analysis technique. The ICP method and the topology matching method cited above can be used as the analysis technique.

LIST OF REFERENCE NUMERALS OR CHARACTERS 1 recording apparatus
1.1-1.3 position
2.1-2.4 light sources
3.1-3.4 diaphragm units
4.1-4.4 deflecting means
5 mirror
6 CCD sensor
6.1 CCD sensor
6.2 CCD sensor
7.1-7.4 projected beams
8 object
9 triangulation plane
10.1-10.4 slits
11.1-11.4 pattern
12.1-12.4 stripes
13.1-13.4 monitoring beams
14 triangulation angle
15 evaluation unit
16 display device
17 operating unit
19 measurement range
20 triangulation image
20.1-20.4 triangulation image
21 3D model, 3D data set
21.1 3D model, 3D data set
22 direction
22.2 direction
23 common 3D image
30 direction of projection
30.1-30.4 direction of projection
31 monitoring direction
40 direction of projection
41 direction of projection
42 angle between the directions of projection
50 monitoring direction
51 monitoring direction
52 angle between the monitoring directions
53 triangulation image
54 triangulation image
60 position on the stripe
61 position on the stripe
62 position on the stripe
63 position on the stripe

What is claimed is:

1. A method for optically measuring a three-dimensional geometry of an object using a triangulation method of a dental intraoral camera including at least one light source, at least one diaphragm unit for producing structured patterns, and at least one recording unit, the method comprising:
    producing a first pattern by a first diaphragm unit and projecting the first pattern onto the object to be measured as a first projected beam; and
    producing a further pattern by at least one further diaphragm unit and projecting the further pattern onto the object to be measured as a further projected beam,
    wherein said first pattern and said further pattern are back-projected from said object as monitoring beams;
    imaging said monitoring beams, by the at least one recording unit; and
    acquiring a three-dimensional (3D) data set of said object;
    simultaneously imaging said projected first pattern and said further pattern; and
    storing at least one triangulation image using said at least one recording unit.

2. The method as defined in claim 1, wherein said first pattern and said further pattern are projected onto said object as projected beams in a common direction of projection.

3. The method as defined in claim 1, wherein said monitoring beams of said patterns are imaged from at least two monitoring directions, the first monitoring direction being offset from the other monitoring direction by an angle.

4. The method as defined in claim 3, wherein said monitoring beams of said patterns are imaged by means of a plurality of recording units from different monitoring directions to give a plurality of individual triangulation images.

5. The method as defined in claim 1, wherein said projected beams of said patterns are projected onto said object from at least two different directions of projection and that said monitoring beams of said patterns are imaged from a single monitoring direction, said first direction of projection being offset from said other direction of projection by an angle.

6. The method as defined in claim 1, wherein individual patterns are coded for differentiation of the individual patterns and for identification of the individual patterns in the at least one triangulation image.

7. The method as defined in claim 6, wherein said individual patterns are color-coded by providing said first pattern with a first wavelength and said further pattern with a different wavelength, at least one color sensor being included with one of said at least one recording units, a range of measurement of the at least one color sensor covering wavelengths of said patterns, and wherein differently colored patterns are analyzed separately.

8. The method as defined in claim 6, wherein the individual patterns are provided with a binary gray-scale code and the individual patterns in the at least one triangulation image are identified with reference to said gray-scale code.

9. The method as defined in claim 1, wherein said projected beams of said patterns are projected onto said object from at least two different directions of projection and that said monitoring beams of said patterns are imaged from at least two different monitoring directions.

10. The method as defined in claim 5, wherein a first direction of projection of said first pattern is at an angle of more than 10° to a further direction of projection of said further pattern.

11. The method as defined in claim 3, wherein said first monitoring direction is at an angle of more than 10° to a further monitoring direction, and analyzing of the at least one triangulation image is effected by a stripe projection method based on the triangulation method.

12. The method as defined in claim 3, wherein, in addition to said triangulation images, supplementary images based on a principle of photogrammetry are created of said object from different monitoring directions and are taken into account in analyzing of said triangulation images.

13. The method as defined in claim 12, wherein both the analyzing of said triangulation images on a principle of stripe projection and the analyzing of said supplementary images on the principle of photogrammetry are effected by an evaluation unit.

14. The method as defined in claim 1, wherein the at least one recording unit include at least one CCD sensor.

15. The method as defined in claim 1, wherein an evaluation unit generates 3D data of each of a plurality of imaged regions of said object in a plurality of individual triangulation images and combines the 3D data generated to form the 3D data set of said object.

16. The method as defined in claim 15, wherein a display unit graphically displays the 3D data set of said object as a graphical 3D model.

17. The method as defined in claim 1, wherein, when use is made of a stripe projection method, individual patterns are formed by a plurality of parallel stripes.

18. The method as defined in claim 3, wherein at least two triangulation images created from different monitoring directions are analyzed, the at least two triangulation images being superimposed with reference to a plurality of matching regions, and an analytical procedure used for detecting said matching regions is an Iterative Closest Point (ICP) method or a topology-matching method.

19. The method as defined in claim 1, wherein 3D data are acquired exclusively by the analyzing of said patterns of the at least one triangulation image, individual stripes are identified by counting said stripes or by a method involving a binary code.

20. The method as defined in claim 1, wherein 3D data of each of the at least one triangulation image are generated by analyzing at least four phase-varying patterns in the at least one triangulation image.

21. The method as defined in claim 1, wherein projection means concurrently projects at least two patterns onto said object.

22. The method as defined in claim 1, wherein, in a first step, a first group of patterns is simultaneously imaged to give at least one first triangulation image using the at least one recording unit, and, in another step following a fixed time interval, a further group of patterns is simultaneously imaged to give at least one further triangulation image, a position of said dental intraoral camera relative to said object to be scanned being changed during said time interval.

23. The method as defined in claim 22, wherein, from said first group of patterns in said at least one first triangulation image, a first 3D data set of said object is obtained and, from the further group of patterns in said at least one further triangulation image, a further 3D data set of said object is obtained, and then said first 3D data set and said further 3D data set are combined to form a common 3D image of said object.

* * * * *